(12) United States Patent  
Shelton et al.

(10) Patent No.: US 10,278,570 B2  
(45) Date of Patent: May 7, 2019

(54) OTOSCOPE TIP AND METHODS OF USE

(71) Applicant: PhotoniCare, Inc., Champaign, IL (US)

(72) Inventors: Ryan Shelton, Champaign, IL (US); Ryan Nolan, Urbana, IL (US)

(73) Assignee: PhotoniCare, Inc., Champaign, IL (US)

( * ) Notice: Subject to any disclaimer, the term of this patent is extended or adjusted under 35 U.S.C. 154(b) by 0 days.

(21) Appl. No.: 15/806,653

(22) Filed: Nov. 8, 2017

(65) Prior Publication Data

US 2018/0125346 A1    May 10, 2018

Related U.S. Application Data

(63) Continuation of application No. PCT/US2016/031450, filed on May 9, 2016.

(60) Provisional application No. 62/158,765, filed on May 8, 2015.

(51) Int. Cl.
| | |
|---|---|
| *A61B 1/227* | (2006.01) |
| *A61B 1/00* | (2006.01) |
| *A61B 1/32* | (2006.01) |

(52) U.S. Cl.
CPC ........ *A61B 1/2275* (2013.01); *A61B 1/00101* (2013.01); *A61B 1/00128* (2013.01); *A61B 1/00135* (2013.01); *A61B 1/00142* (2013.01); *A61B 1/32* (2013.01)

(58) Field of Classification Search
CPC ............................. A61B 1/227; A61B 1/2275
See application file for complete search history.

(56) References Cited

U.S. PATENT DOCUMENTS

| | | | |
|---|---|---|---|
| 3,110,304 A | 11/1963 | Hartman | 128/9 |
| 4,380,998 A | 4/1983 | Kieffer, III et al. | 128/9 |
| 5,491,524 A | 2/1996 | Hellmuth et al. | 351/212 |
| 5,836,877 A | 11/1998 | Zavislan | 600/407 |
| 5,919,130 A * | 7/1999 | Monroe | A61B 1/227 600/129 |
| 5,921,926 A | 7/1999 | Rolland et al. | 600/407 |
| 5,994,690 A | 11/1999 | Kulkarni et al. | 250/216 |
| 7,289,842 B2 | 10/2007 | Maschke | 600/478 |
| 7,354,399 B2 | 4/2008 | Strom et al. | 600/200 |
| 7,406,346 B2 | 7/2008 | Kleen et al. | 600/424 |
| 7,949,385 B2 | 5/2011 | Khamene et al. | 600/416 |
| 8,115,934 B2 | 2/2012 | Boppart et al. | 356/479 |
| 8,135,453 B2 | 3/2012 | Slabaugh et al. | 600/473 |
| 8,197,403 B2 | 6/2012 | Strom et al. | 600/184 |
| 8,594,757 B2 | 11/2013 | Boppart et al. | 600/310 |

(Continued)

FOREIGN PATENT DOCUMENTS

| | | | |
|---|---|---|---|
| KR | 1013443040000 | 12/2013 | A61C 1/08 |

OTHER PUBLICATIONS

Translation to English of KR 101344304 (also identified as KR 20130095361); accessed from the EPO on Sep. 13, 2018.*

(Continued)

*Primary Examiner* — Julianna N Harvey

(74) *Attorney, Agent, or Firm* — J. Peter Paredes; David G. Rosenbaum; Rosenbaum IP, P.C.

(57) ABSTRACT

Provided herein are systems, methods, and designs of speculum tips for pneumatic otoscopy. A speculum tip is disclosed and generally comprises: a cylindrical configuration including a narrow distal tip region longitudinally extending from a larger proximal region.

20 Claims, 13 Drawing Sheets

(56) References Cited

U.S. PATENT DOCUMENTS

| | | | |
|---|---|---|---|
| 2009/0185191 A1* | 7/2009 | Boppart | A61B 5/0066 356/479 |
| 2013/0060131 A1 | 3/2013 | Oghalai et al. | 600/425 |
| 2013/0214054 A1 | 8/2013 | Faulkner et al. | B05B 5/03 |
| 2013/0289353 A1 | 10/2013 | Seth et al. | A61B 1/277 |
| 2013/0300919 A1 | 11/2013 | Fletcher et al. | H04N 5/2254 |
| 2014/0012141 A1 | 1/2014 | Kim et al. | A61B 1/227 |
| 2018/0078120 A1* | 3/2018 | Poll | A61B 1/0008 |

OTHER PUBLICATIONS

International Preliminary Report on Patentability, PCT Application No. PCT/US2016/031450, pp. 1-6 (dated Nov. 23, 2017).

American Academy of Otolaryngology—Head and Neck Surgery. Fact Sheet: Ear Infection and Vaccines, 2014. https://www.entnet.org/HealthInformation/earInfectionVaccines.cfm.

Klein, J. O., Otitis Media Clinical Infectious Diseases, vol. 19, No. 5: pp. 823-833, Nov. 1994.

Bartelds, A.I.M. et al., Acute Otitis Media in Adults: A Report From the International Primary Care Network. J Am Board Fam Pract, vol. 6, No. 4: pp. 333-339, Jul.-Aug. 1993.

Roberts J.E. et al., Ear Infections and Language Development. U.S. Dept. of Education, DOE Publication No. ECI-2000-9008, 2000.

Monasta, L. et al., Burden of Disease Caused by Otitis Media: Systematic Review and Global Estimates. PLoS One, vol. 7, Issue 4, e36226, Apr. 2012.

Hsu, G.S., et al., Management of otitis media using Agency for Health Care Policy and Research guidelines. The Agency for Health Care Policy and Research. Otolaryngology—Head Neck Surg, vol. 118, No. 4: pp. 437-443, Apr. 1998.

Lieberthal, A.S., et al., The Diagnosis and Management of Acute Otitis Media. Pediatrics, vol. 131, No. 3: e964-99, Mar. 2013.

Jones W.S., et al., How Helpful Is Pneumatic Otoscopy in Improving Diagnostic Accuracy? Pediatrics, vol. 112, No. 3; pp. 510-513. Sep. 2003.

Morris E, et al., Development and Validation of a Novel Ear Simulator to Teach Pneumatic Otoscopy. Simulation in Healthcare. vol. 7, No. 1, pp. 22-26. Feb. 2012.

Shekelle, G.T., et al, Diagnosis, Natural History, and Late Effects of Otitis Media with Effusion. Evidence Reports/Technology Assessments, No. 55, Sections 1 and 4, 2002.

Burrows, H.L., Otitis Media, Guidelines for Clinical Care Ambulatory, UMHS Otitis Media Guideline. Apr. 2013.

Hawkins, M., A Survey of America's Physicians: Practice Patterns and Perspectives. The Physicians Foundation, Sep. 2012.

Subcommittee on Management of Acute Otitis Media. Diagnosis and Management of Acute Otitis Media, Pediatrics, vol. 113, No. 5: pp. 1451-1465, 2004.

Centers for Disease Control and Prevention. *Ambulatory Care Use and Physician Visits*. Available: http://www.cdc.gov/nchs/fastats/docvisit.htm (2012, Sep. 15, 2012).

D'Eredità, R., Porcine small intestinal submucosa (SIS) myringoplasty in children: A randomized controlled study, Int. J. Pediatr. Otorhinolaryngol. 79: pp. 1085-1089 (2015).

http://www.gtzip.com/helpfaqs.html, Accessed Feb. 12, 2016.

http://www.plastifab.ca/a-upload-pdfs/13_01.pdf, Accessed Feb. 12, 2016.

Krueger, P.S. et al., Vortex Rings in Bio-inspired and Biological Jet Propulsion, Advances in Science and Technology, vol. 58: 237-246 (Sep. 2, 2008).

Shi, L. et al., Biochemical and biomechanical characterization of porcine small intestinal submucosa (SIS): a mini review, Int J Burn Trauma,pp. 2013;3(4): 173-179 (Nov. 15, 2013).

Volandri, G. et al., Biomechanics of the tympanic membrane, Journal of Biomechanics. 44: pp. 1219-1236 (2011).

\* cited by examiner

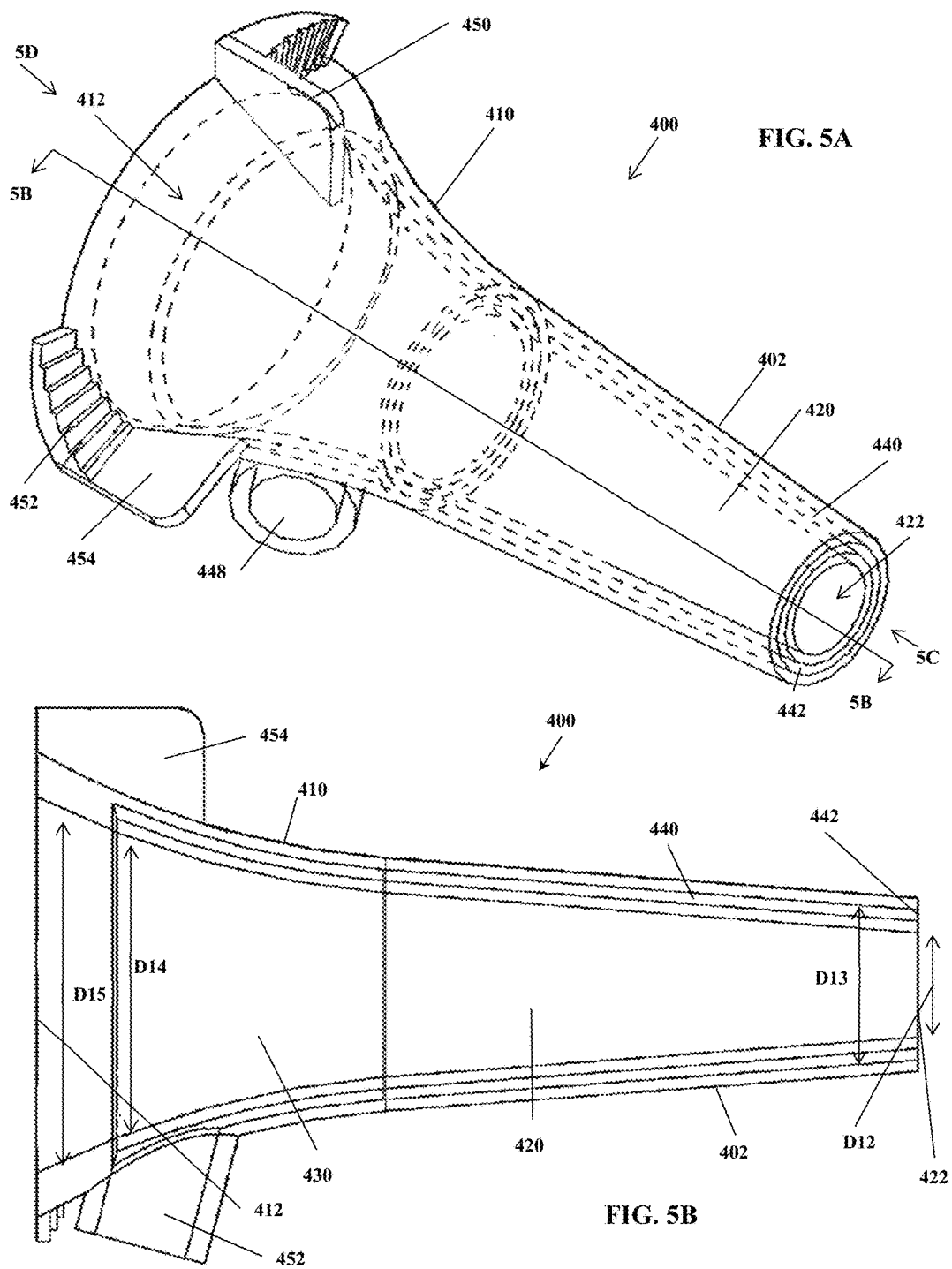

OTOSCOPE TIP AND METHODS OF USE

CROSS-REFERENCE TO RELATED APPLICATIONS

The present application claims priority to and is a continuation from PCT application serial no. PCT/US2016/031450, which is filed May 9, 2016; which claims priority from U.S. provisional application Ser. No. 62/158,765, filed May 8, 2015, all herein incorporated by their entireties.

BACKGROUND

The invention generally relates to the field of otoscopy and in particular to an improved otoscopic tip element for use with otoscopic apparatus.

Ear infections are the leading cause of hearing loss and most common reason for surgery in children. They are responsible for 30M visits to physicians each year in the U.S. and represent a nearly $10 B burden on the U.S. economy. The American Academy of Pediatrics (AAP) and the American Academy of Otolaryngology (AAO) recommend pneumatic otoscopy as the gold standard for diagnosing this disease, wherein a change in pressure is delivered to the ear canal to modulate the eardrum; however, very few physicians perform the exam correctly due to difficulty establishing a seal of the ear canal.

The current gold standard for diagnosing middle ear infections is otoscopy, where a lens is used to visually examine the surface of the tympanic membrane (TM), or eardrum. However, this exam is highly subjective, with misdiagnosis rates of up to 50% amongst typical physicians. The addition of pneumatic otoscopy to the standard exam can increase the accuracy of the exam to 90%, and is part of the recommended guidelines developed by the American Academy of Pediatrics (AAP) and the American Academy of Otolaryngology (AAO). Pneumatic otoscopy, or the use of a traditional otoscope supplemented with an insufflation bulb, allows the physician to control the pressure in the ear canal to induce deflections of the TM. A physician then observes the deflection behavior of the TM to deduce the presence or absence of an effusion in the middle ear. However, this additional exam is rarely performed correctly because it is very difficult to obtain a sufficient seal of the ear canal using the current otoscope and speculum technology on the market.

Current disposable specula make it difficult to obtain a seal of the ear canal, and even products designed for pneumatic use perform very poorly due to the use of hard rubber material and non-ideal geometry. Currently, the most commonly used specula are standard tips in 4.2 mm (adult) or 2.7 mm (pediatric) sizes. While these tips are good for interfacing with the ear canal and provide access to a surface image of the TM, they are not designed specifically to facilitate sealing of the ear canal for pneumatic otoscopy. As a result, pneumatic otoscopy is rarely performed and even, more importantly, rarely performed accurately. There have been attempts at pneumatic-specific specula tips, such as the SofSeal and SofSpec from Welch Allyn, but these products do not seal the ear canal significantly better than standard tips, which explain the poor adoption of the SofSeal specula by physicians. The SofSeal uses a hard rubber, which does not seal well with the ear canal.

Correct performance and evaluation of a pneumatic otoscope exam alongside a traditional otoscope exam increases diagnostic accuracy of otitis media (OM) from 50% to better than 90% amongst experienced users, and it is the strongest diagnostic recommendation from AAP and AAO for OM. Despite this strong recommendation from the guideline providers, less than 50% of physicians utilize pneumatic otoscopy as part of their normal patient exam, and 43% of pneumatic otoscope exams are performed or interpreted incorrectly. The biggest reason for the poor adoption and use of this technique is the difficulty associated with obtaining a seal of the ear canal. Sealing the ear canal is currently a requirement to perform pneumatic otoscopy, and it can be very difficult to achieve with current tools and in the presence of uncooperative pediatric patients. The present invention attempts to solve these problems, as well as others.

SUMMARY OF THE INVENTION

Provided herein are systems, methods, and designs of speculum tips for pneumatic otoscopy. A speculum tip is disclosed and generally comprises: a cylindrical configuration including a narrow distal tip region longitudinally extending from a larger proximal region, wherein the distal tip region generates a toroidal vortex throughout a central shaft lumen coaxially disposed within the distal tip region; a distal end of the central shaft lumen includes a distal opening from which the toroidal vortex travels to displace a membrane; the proximal region includes a proximal opening operably coupled with a proximal lumen coaxially disposed within the proximal region as to receive a pulse of fluid.

A method of generating a toroidal vortex for a speculum tip is disclosed and comprises: generating a toroidal vortex through speculum tip comprising a cylindrical configuration with a narrow distal tip region longitudinally extending from a larger proximal region; passing a pulse of fluid through a generally central shaft lumen coaxially disposed within the distal tip region and a distal opening on a distal end of the central shaft lumen; and displacing a membrane by the toroidal vortex exiting the distal opening without the requirement of a pressure seal of the ear canal.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 5A is a perspective view of one embodiment of the speculum tip.

FIG. 5B is a cross-sectional view of one embodiment of the speculum tip taken along line 5B-5B from FIG. 5A.

DETAILED DESCRIPTION OF THE INVENTION

Figure 1A:
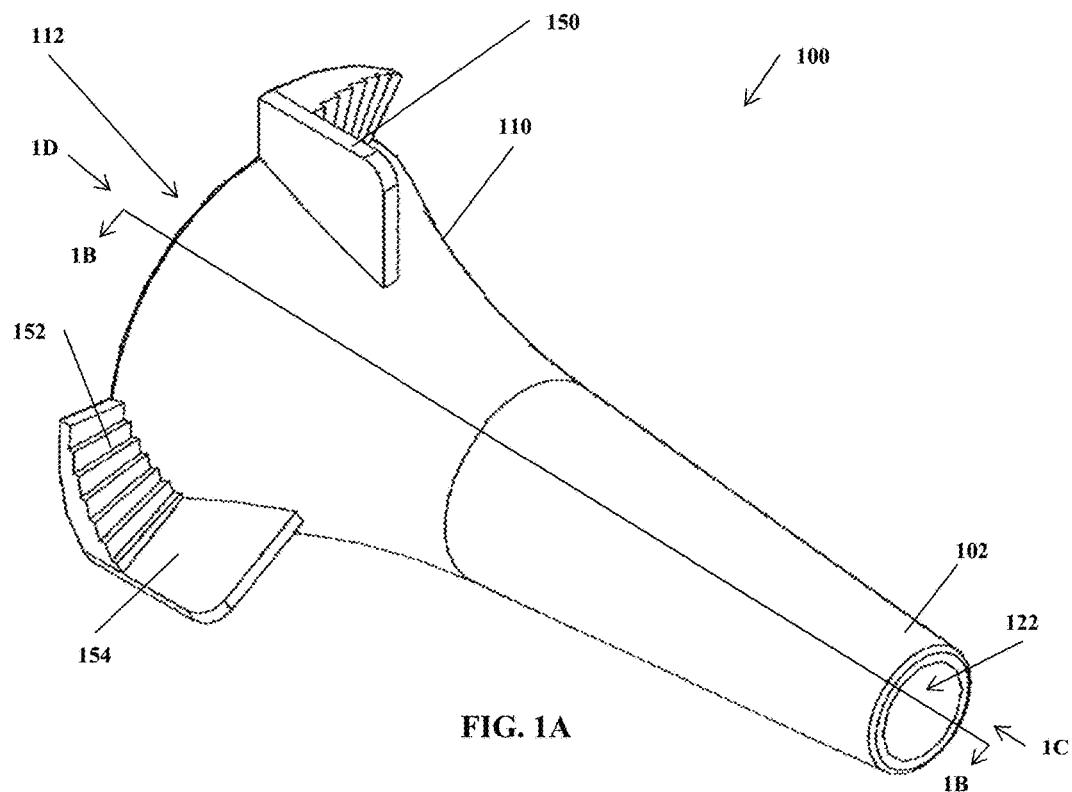
FIG. 1A is a perspective view of one embodiment of the speculum tip.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant or the patient anatomy to be examined.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant, both in relation to the other endpoint, and independently of the other endpoint.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The speculum tip disclosed herein significantly improves physicians' abilities to efficiently perform this crucial exam. Increasing the use of pneumatic otoscopy will lead to better diagnostic decisions, which will ensure more appropriate prescription of antibiotics and better decisions for surgical intervention. Embodiments of the disposable specula tips used for otoscopy will provide two new features as separate products: (1) enable a quick and easy seal of the ear canal; and (2) deliver the pneumatic insufflation air puff in such a way that a seal of the ear canal is not required. These features will ultimately help the physicians make a more accurate diagnosis and more closely adhere to the AAP and AAO guidelines, resulting in better treatment decisions and less waste.

In one embodiment, a speculum tip is disclosed that allows a quick and easy seal of the ear canal. The speculum tips disclosed herein obviates the need to obtain a seal of the ear canal by delivery of the insufflation stimulus through a specially designed otoscope speculum tip. The speculum tips employ a toroidal vortex fluid to optimize air delivery and facilitate use of pneumatic otoscopy in order to improve compliance with AAP and AAO guidelines for patient care. Alternatively, the speculum tips may incorporate a quick and easy seal of the ear canal by simply inserting the speculum tip into the patient's ear. The speculum tips generate a toroidal vortex to displace the TM, such that physicians can detect changes in TM modulation when making their assessment and diagnosis with the current commercial otoscopy technology. Due to the variation in ear canal and eardrum anatomy, physicians employ different sizes of specula. Small (2.7 mm) diameter speculum tips are used on infants and very young children, while larger (4.2 mm) diameter speculum tips are used on older children and adults. Alternatively, different diameter speculum tips may be provided according to the anatomy of the ear canal or other organ being examined. Alternatively, the speculum tip may be used for other membrane displacement applications, including a tonometer in ophthalmology to displace the eye.

The toroid delivery and dynamic interaction with the eardrum initiates modulation for pneumatic otoscopy. From a thermodynamics view, the toroid vortex can be considered as an impulse or transformation of energy to the eardrum, delivered by the expelled fluid from the distal end of the speculum tip, at which point the interaction with the static air in the ear canal produces the toroid vortex. The impulse energy delivered can be thermodynamically described and related in terms of a pressure or force upon the eardrum to illicit modulation, as shown in EQS. 1-2.

Ideal Gas Law:

$$p = \frac{nRT}{V};  \quad (1)$$

where p is pressure, n is number of moles of gas, R is the gas constant, T is temperature, and V is volume. For our application, n, R, and T remain ambiently constant while V, and consequently p, change upon pneumatic insufflation.

Force: pressure relationship: $F = p \times A;$ (2)

where F is the normal force (applied perpendicular to the surface), p is pressure, and A is the surface area. For our application, the A is the surface area of the eardrum to be modulated. This conversion of pressure into force can be used to derive the incident force applied on the eardrum by the toroid vortex.

Impulse (I) is defined as the product of Force (F) times Time (T) for which it is applied. The toroid may include an impulse.

Considering the pneumatic otoscope and ear canal as a thermodynamic system, introduction of pneumatic insufflation impulse through external work, such as volume compression during dynamic impulse delivery, causes an increase in internal energy. In terms of the First Law of Thermodynamics, the energy introduced into the system must be conserved, and thereby introduction of a pneumatic insufflation impulse will result in the modulation of the eardrum (the most pliant of the middle ear tissues), escape through lossy leaks where a seal of the canal is not achieved, or varying degrees of both. Due to inherent difficulty in obtaining a perfect seal of the ear canal, the speculum tip circumvents the need for a seal by delivering a more specialized pneumatic insufflation impulse that will retain more of the initial impulse energy delivered by the user until interaction with the eardrum occurs.

Figure 1B:
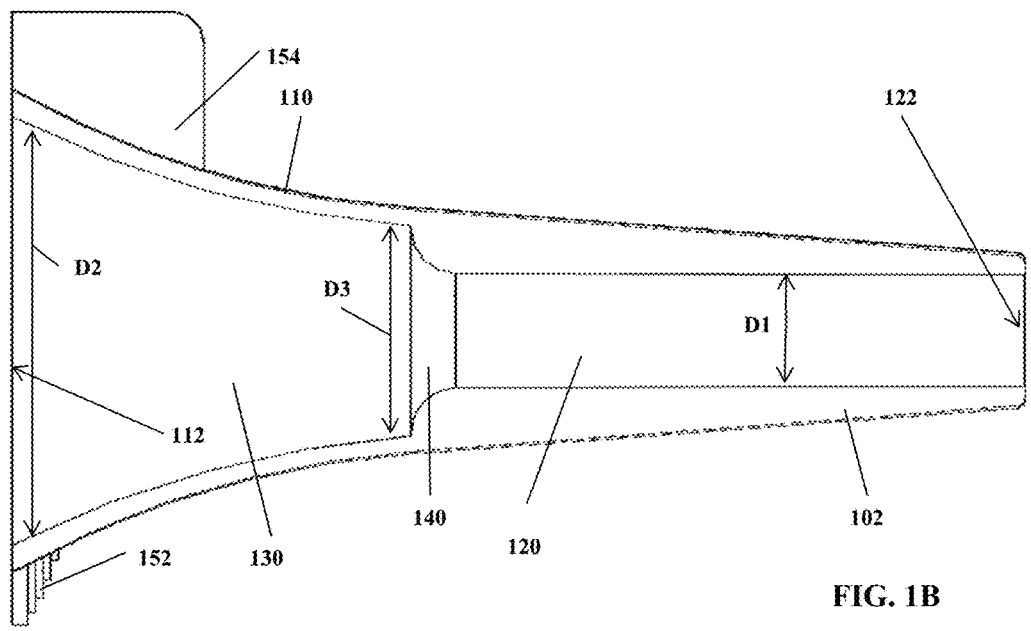
FIG. 1B is a cross-sectional view of one embodiment of the speculum tip taken along line 1B-1B from FIG. 1A.
Figure 1C:
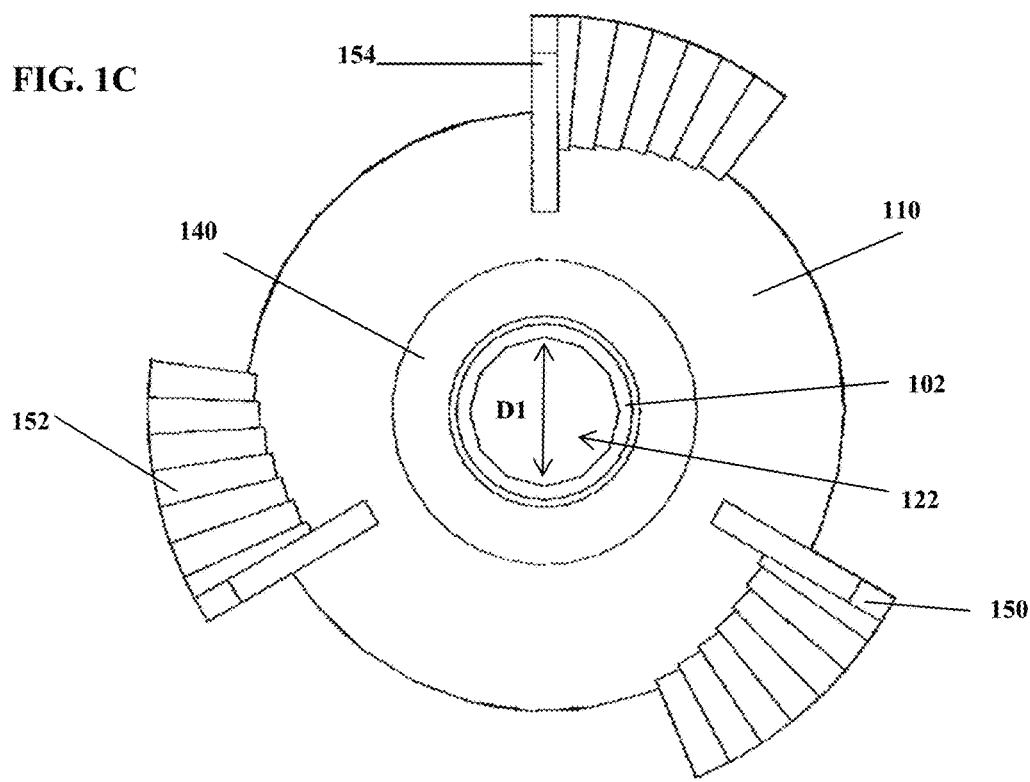
FIG. 1C is a front view of one embodiment of the speculum tip taken from view 1C from FIG. 1A.

Generally speaking, one embodiment of the speculum tip 100 is shown in FIGS. 1A-1D. The speculum tip 100 includes a generally conical configuration with a narrow distal tip region 102 longitudinally extending from a larger proximal region 110. The distal tip region 102 generates a toroidal vortex throughout a generally central shaft lumen 120 coaxially disposed within the distal tip region 102, as shown in FIG. 1B-1C. The distal end of the central shaft lumen 120 includes a distal opening 122 through which the toroidal vortex sufficiently displaces the eardrum without the requirement of a pressure seal of the ear canal. The proximal region 110 includes a proximal opening 112 operably coupled with a proximal lumen 130 disposed within the proximal region 110. The proximal lumen 130 includes a conical or a cylindrical cross-section or profile that narrows to a middle lumen 140, whereby the middle lumen 140 transitions to the central shaft lumen 120. The speculum tip 100 includes a plurality of flanges 150 surrounding the proximal end of the proximal region 110. The flanges 150 include a stepped portion 152 descending from the vertical lip 154. The flanges 150 are used to secure the speculum tip to an otoscope, as to provide the user a grip-like structure to twist or rotate the speculum tip 100 about its longitudinal axis. The flanges 150 may be removed from the speculum tip 100 depending on the otoscope features for securement.

Figure 1D:
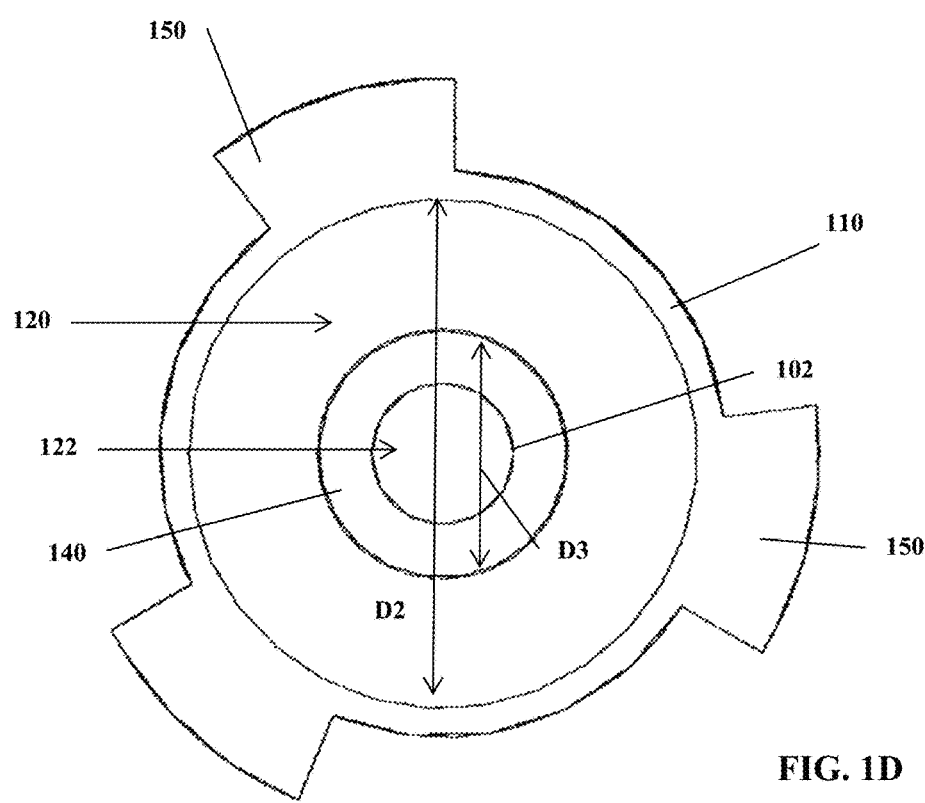
FIG. 1D is a back view of one embodiment of the speculum tip taken from view 1D from FIG. 1A.

In one embodiment, the walls of the central shaft lumen 120 are separated by about 0.1 to about 15 mm as to create the air vortex rings exiting the distal opening 122. As such, the central shaft lumen 120 includes a diameter D1, as shown in FIGS. 1B-1D. The diameter D1 produces a medium sized toroidal vortex or a constant toroidal vortex, as indicated below. The proximal lumen 130 includes a proximal end with a diameter of D2 and the proximal lumen 130 includes a distal end with a diameter of D3. The diameter D2 is larger or greater than the diameter D3, such that the proximal lumen 130 includes a generally curved cross-section shape or profile. The middle lumen 140 includes a proximal end that substantially aligns with the distal end of the proximal lumen 110. The middle lumen 140 includes a distal end that substantially aligns with the proximal end of the central shaft lumen 120. The toroidal vortex is generated by fluid passing through the proximal lumen 130, traversing the middle lumen 140, and exiting the central shaft lumen 120. In one embodiment, the diameter D2 is formatted as to fit a pneumatic otoscope. In one embodiment, the shaft lumen 120 includes a length sufficient and a bolus of injected air to generate the toroidal vortex, as indicated below. The pneumatic otoscope may be operably coupled to a pressure generator to generate the pulse of fluid within the speculum tip. The pressure generator can be manual, automated, and the like. In one embodiment, the pressure generator is a pump, a bulb, or other method of fluid displacement.

Figure 2A:
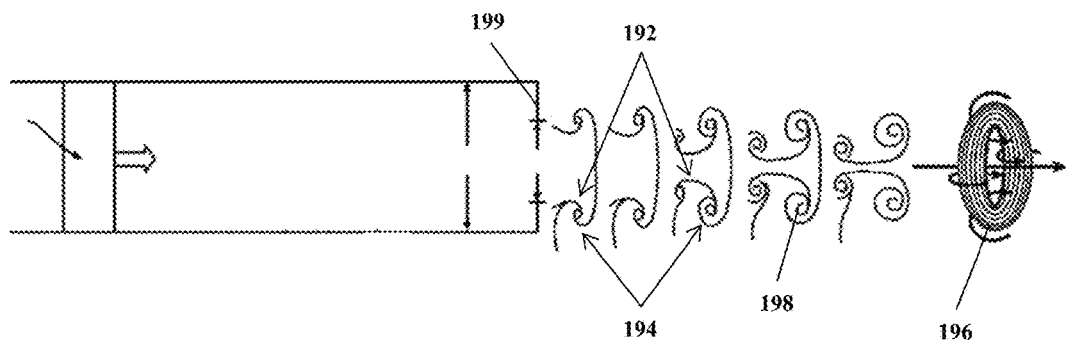
FIG. 2A is a schematic side view of one embodiment of the toroidal vortex.
Figure 2B:
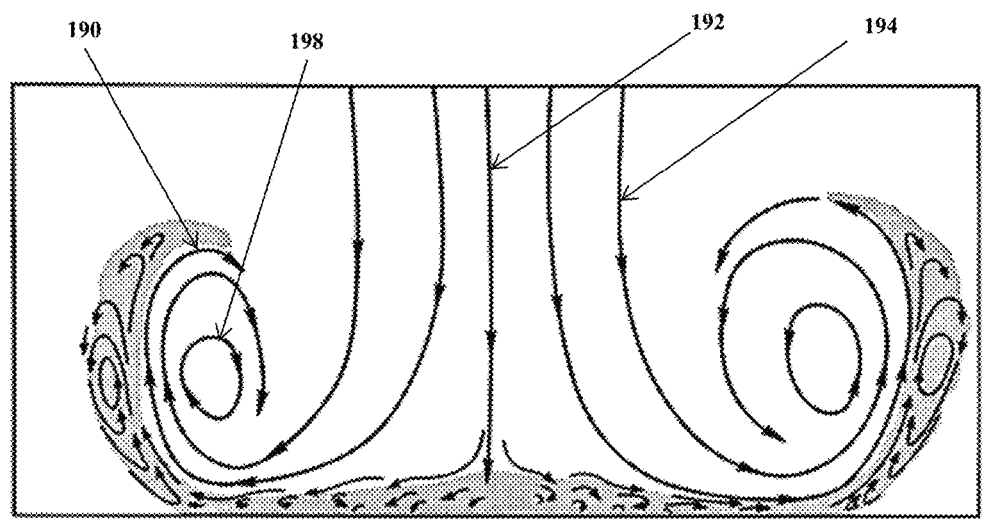
FIG. 2B is a schematic side view of one embodiment of the toroidal vortex.
Figure 2C:
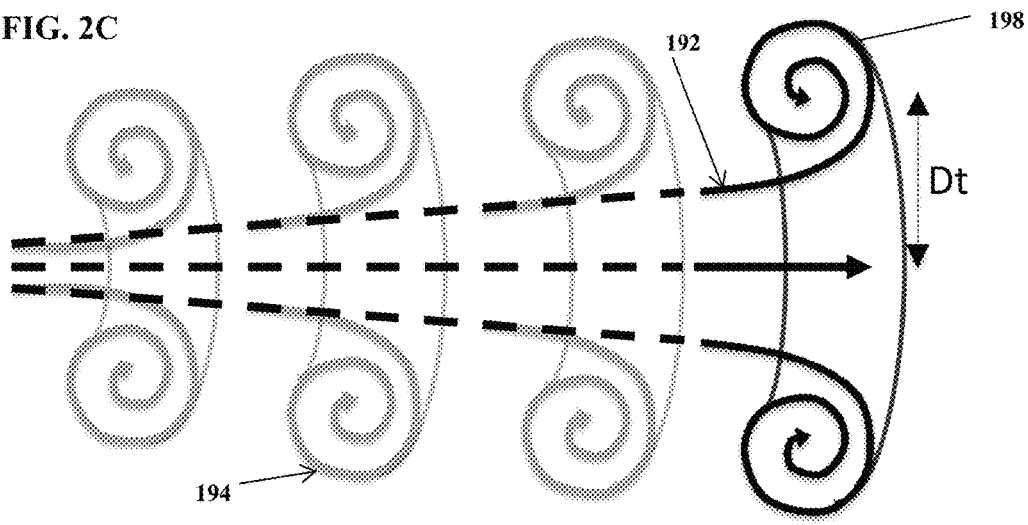
FIG. 2C is a schematic side view of an expanding toroidal vortex.
Figure 2D:
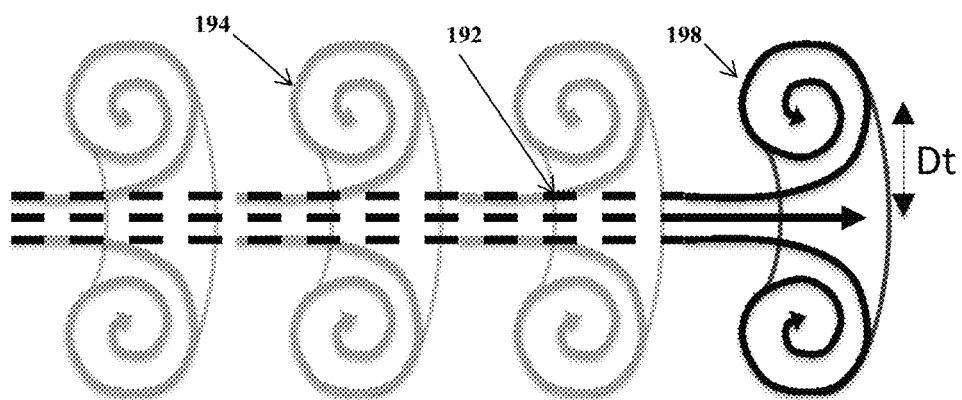
FIG. 2D is a schematic side view of a constant diameter toroidal vortex.
Figure 2E:
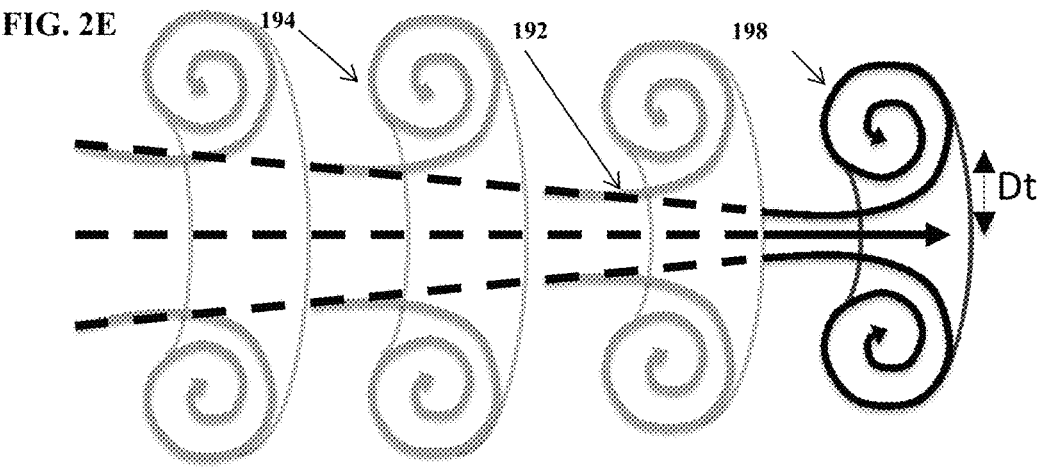
FIG. 2E is a schematic side view of a focusing toroidal vortex.

For the toroidal vortex, a fluid (either air or liquid) is expelled in such a way that a torus-shaped vortex 196 is created out of the central shaft lumen and exiting the distal opening, because the inner edge 192 of the ring 196 moves faster than the outer edge 194, as shown in FIGS. 2A-2B. This vortex ring 196 travels in a perpendicular direction to the plane of the ring, allowing it to carry the spinning fluid 198 and travel much further than simple expulsion (see FIG. 2B). This vortex ring 196 displaces the eardrum without a need to seal the canal due to the more specialized and less lossy impulse pressure/force exerted by the vortex ring structure 196. Several designs disclosed herein may be used to generate toroidal vortices, as shown in the several embodiments of the speculum tips. FIGS. 2A-2B show two toroid vortex examples. These examples require a compact mass of fluid to interact with an interface (e.g. air, liquid, flat solid surface) where one is moving much faster relative to the other. In the most prevalent case, as shown in FIG. 2A, a stationary air or liquid environment interface at the distal end of the toroid-generating device 199 causes drag on the outer edge of the expelled, quick, compact fluid mass, which slows down the outer layers of the fluid mass relative to its core. This aerodynamic drag causes the ejected air to begin rotating. When the slower outer layers slip around and collect at the rear, they re-enter the fluid mass in the wake of the faster moving core and form the toroid ring structure. This ring structure is held together by inward pressure because the air inside the toroid ring is moving faster and, according to Bernoulli's law, is lower pressure than the air on the outside. However, the aerodynamic drag eventually overcomes the energy stored in the toroid ring and the ring dissipates. In another case, as shown in FIG. 2B, toroidal vortices can be formed (as in microbursts) when the compact fluid mass collides with a flat stationary wall. When the compact fluid mass hits the wall, the fluid shoots out radially along the wall plane. The toroidal vortex ring is then produced by the viscous friction between the faster layer of outward flow at the wall's surface and the slower fluid mass in its wake. The toroidal vortex utilizes the drag from an interface not perpendicular to the travel of the vortex (FIG. 2A) and generates an initial compact fluid mass with either a highly pressurized source or stretching and releasing an elastic membrane or spring to create an impulse. In one embodiment, the toroidal vortex includes a fluid burst of at least about 5 mmHg to about 100 mmHg. The fluid burst to create this toroidal vortex may be higher than about 5 mmHg to about 100 mmHg. In one embodiment, the toroidal vortex creates a pressure ring of at least about 5 mmHg to about 75 mmHg to displace the TM and analysis of the response is utilized to diagnosis otitis media. In one embodiment, the pressure ring is about 25 mmHg, and the detected motion of the TM may be at least about 5 mmHg, which may be detected by Optical Coherence Tomography (OCT), as further explained below. The toroidal vortex may be an expanding toroidal vortex, whereby the diameter Dt of the toroidal vortex expands as it travels further away from the speculum tip, as shown in FIG. 2C. The toroidal vortex may be a focusing toroidal vortex that may focus the toroidal vortex to a smaller target, as shown in FIG. 2E. Or the toroidal vortex may be a constant toroidal vortex that maintains the same diameter as it travels away from the speculum tip, as shown in FIG. 2D. The toroidal vortex may be a double-concentric toroidal vortex, which is a double-curling air vortex ring. The diameter of the toroidal vortex may be between about 0.5 to about 8.0 mm.

If the pressure is between about 5 mmHg-100 mmHg and the area is about 50 mm$^2$, then by using equation (2) p=F/A=>F=pA=(0.6666 kPa-13.333 kPa)*5e-5 m$^2$=33.3 mN-666.6 mN. Thus, the force of the toroidal vortex may be between about 33.3 mN to about 666.6 mN.

The pressure in the sealed ear canal is slowly changed to observe deflection of the TM, because of the sealed canal, this deflection rate is directly tied to and identical to that of the bulb compression/expansion in the user/physician's hand or other air pressure source. In the embodiments disclosed herein, dynamically loading the TM by the toroidal vortex abruptly pushes the TM, which is detected. The rate for the change in pressure may be between about 35 to about 50 milliseconds, in one embodiment. Dynamically loading the TM is abruptly impacting the TM with finite, discrete pulses/vortices of gas (air, $CO_2$, etc.), which load the TM over a much smaller time scale than current pneumatic otoscopy technique.

Figure 3A:
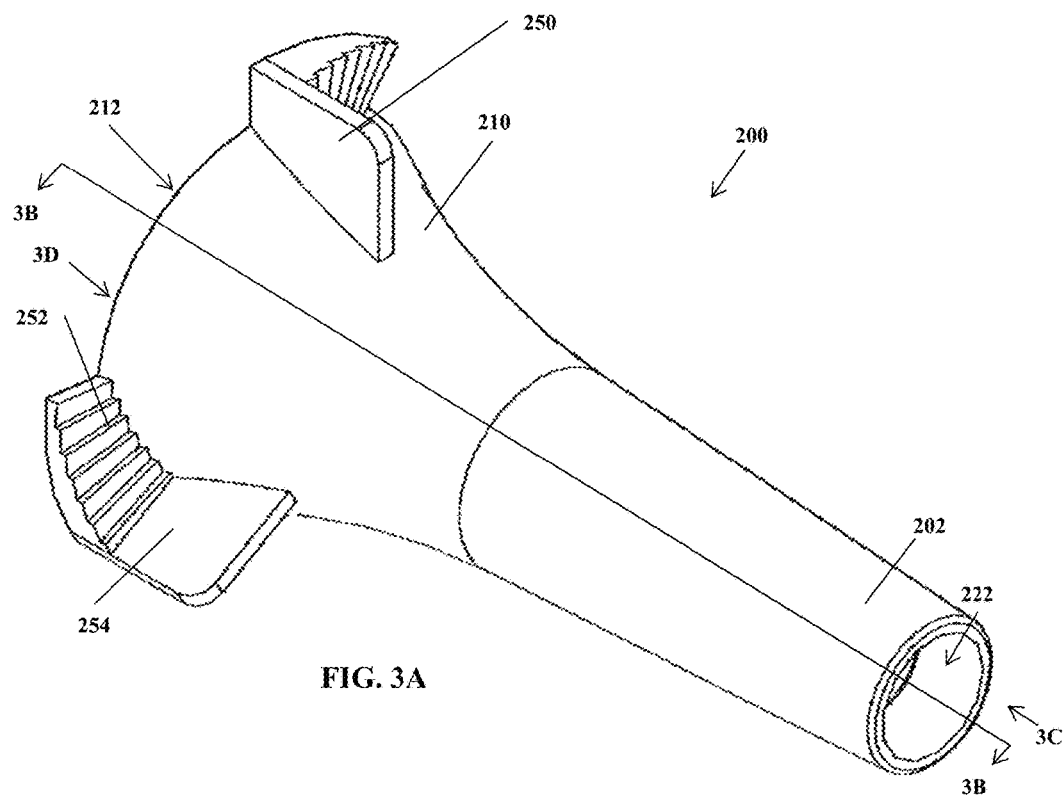
FIG. 3A is a perspective view of one embodiment of the speculum tip.
Figure 3B:
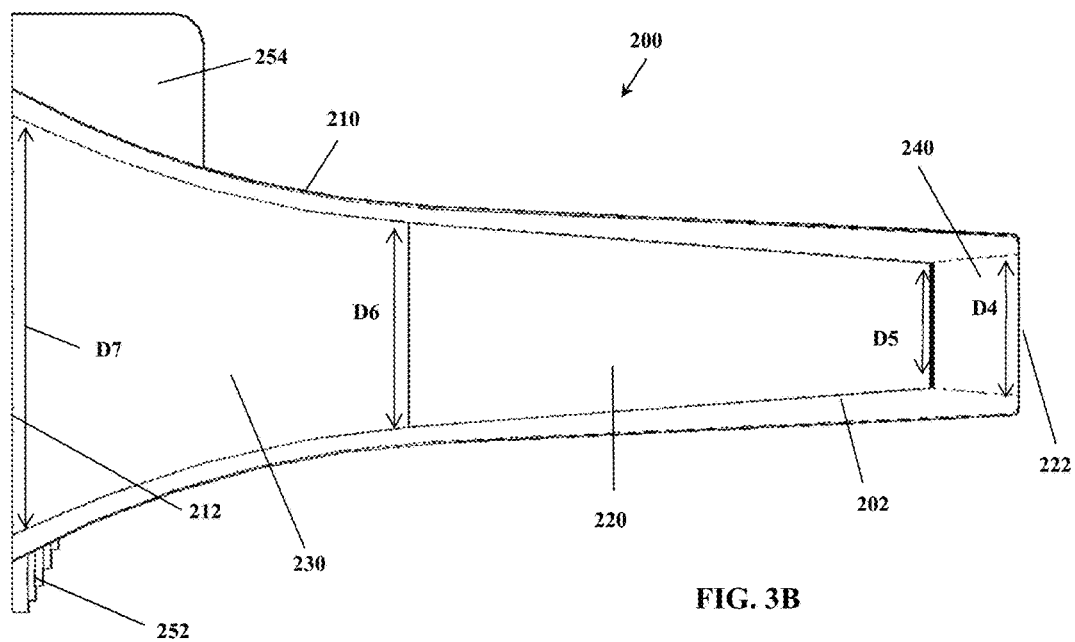
FIG. 3B is a cross-sectional view of one embodiment of the speculum tip taken along line 3B-3B from FIG. 3A.
Figure 3C:
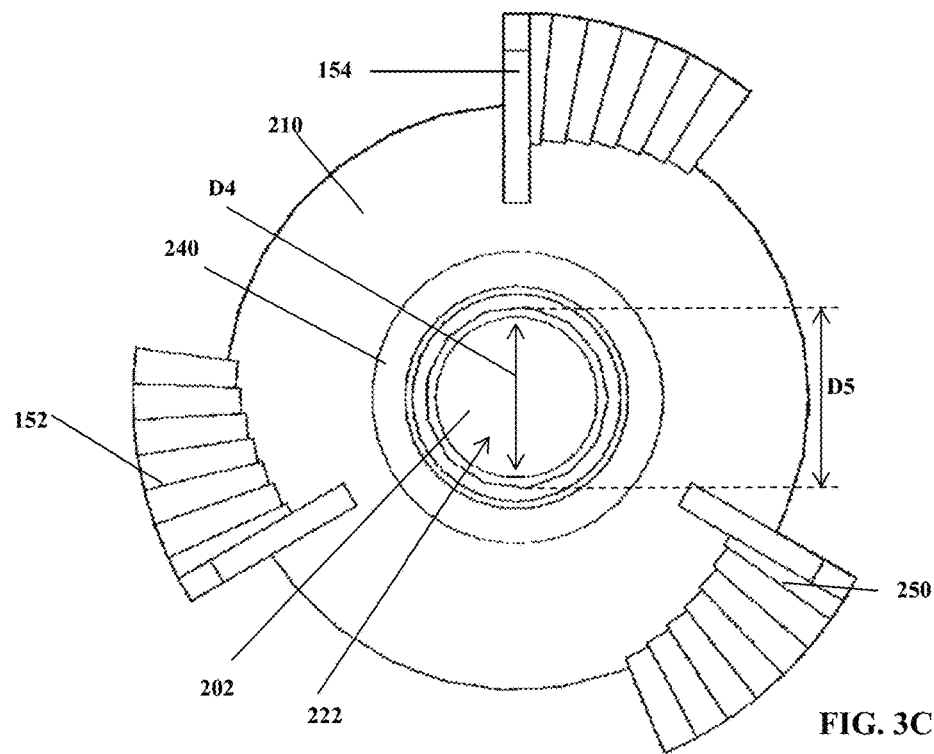
FIG. 3C is a front view of one embodiment of the speculum tip taken from view 3C from FIG. 3A.

Another embodiment of the speculum tip 200 is shown in FIGS. 3A-3D. Similar features and elements are present in the speculum tip 200 as the speculum tip 100 with several slight variations. The speculum tip 200 includes a generally conical configuration with a narrow distal tip region 202 longitudinally extending from a larger proximal region 210. The distal tip region 202 generates a toroidal vortex by fluid traversing through a central shaft lumen 220 and a distal lumen 240 coaxially disposed within the distal tip region 202, as shown in FIG. 3B-3C. The distal end of the central shaft lumen 220 includes a distal end that is coupled to a proximal end of the distal lumen 240. The central shaft lumen 220 includes a conical cross-section or profile that narrows to the distal lumen 240. The distal lumen 240 includes trapezoidal cross-section or profile that includes a distal end larger than a proximal end. The distal end of the distal lumen 240 includes a distal opening 222 through which the toroidal vortex displaces the eardrum without the requirement of a pressure seal of the ear canal. The proximal region 210 includes a proximal opening 212 operably coupled with a proximal lumen 230 disposed within the proximal region 210. The proximal lumen 230 includes a conical cross-section or profile that narrows to the central shaft lumen 220, whereby the central shaft lumen 220 transitions to the distal lumen 240. The speculum tip 200 includes a plurality of flanges 250 surrounding the proximal end of the proximal region 210. The flanges 250 include a stepped portion 252 descending from the vertical lip 254. The flanges 250 are used to secure the speculum tip to an otoscope as to provide the user a grip-like structure to twist or rotate the speculum tip 100 about its longitudinal axis. The flanges 150 may be removed from the speculum tip 100 depending on the otoscope features for securement.

Figure 3D:
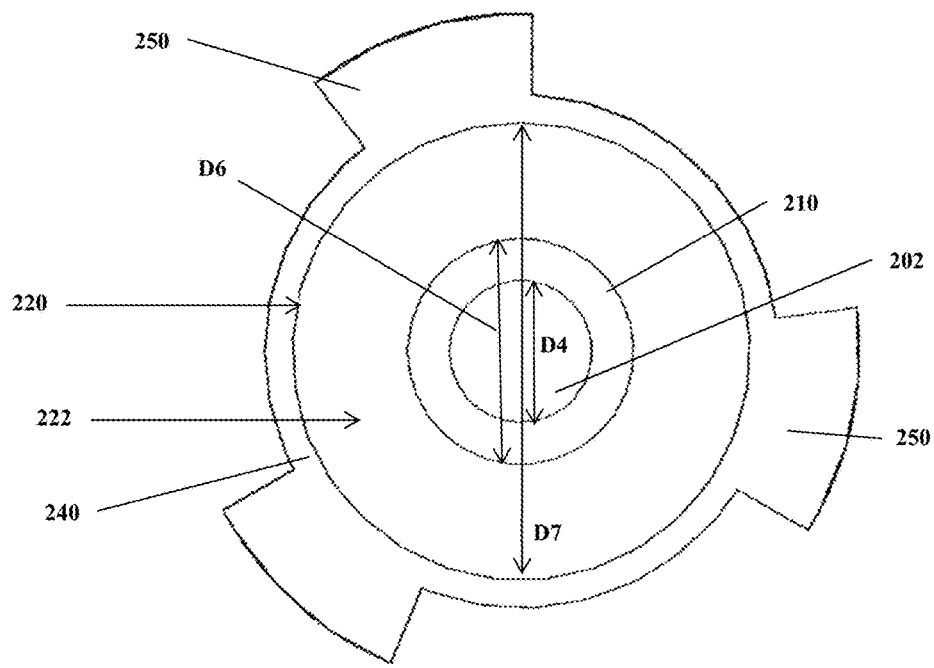
FIG. 3D is a back view of one embodiment of the speculum tip taken from view 3D from FIG. 3A.

In one embodiment, the walls of the central shaft lumen 220 are separated by about 0.5 to about 15 mm as to create the air vortex rings exiting the distal opening 222. The distal lumen 240 includes an expanded tip cross-section or profile, where the distal end of the distal lumen 240 includes a diameter D4 that produces a large-sized or expanding toroidal vortex as indicated previously as shown in FIGS. 3B-3D. As such, the distal end of the central shaft lumen 220 narrows to a diameter D5, wherein the distal end of the central shaft lumen 220 coaxially aligns with the proximal end of the distal lumen 240. The narrowing of the central shaft lumen 220 to diameter D5 causes the vortex diameter to expand rather than maintain the diameter as it travels distally. The diameter D4 is larger than the diameter D5 to produce a large-sized or expanding toroidal vortex through the distal opening 222, after which the toroid ring diameter expands as it travels forward or away from the distal opening 222.

The proximal lumen 230 includes a distal end with a diameter D6 that coaxially aligns with the proximal end of the central shaft lumen 220, as shown in FIGS. 3B-3D. The diameter D6 is larger or greater than the diameter D5 of the distal end of the central shaft lumen 220, such that the central shaft lumen 220 includes a generally trapezoidal cross-section or profile. The proximal lumen 230 includes a proximal end with a diameter of D7. The diameter D7 is larger or greater than the diameter D6 of the distal end of the proximal lumen 230, such that the proximal lumen 230 includes a generally curved cross-section shape or profile. The toroidal vortex is generated by fluid passing through the proximal lumen 230, traversing the central shaft lumen 220, and exiting the distal lumen 220 and distal opening 222.

Figure 4A:
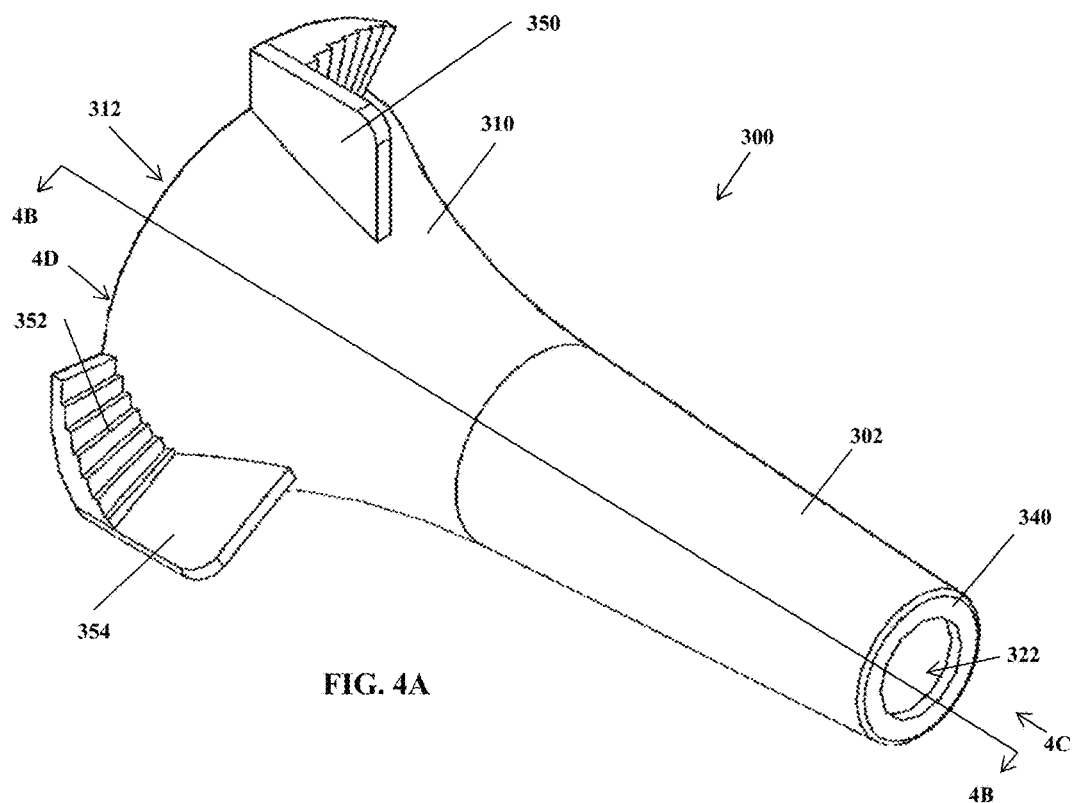
FIG. 4A is a perspective view of one embodiment of the speculum tip.
Figure 4B:
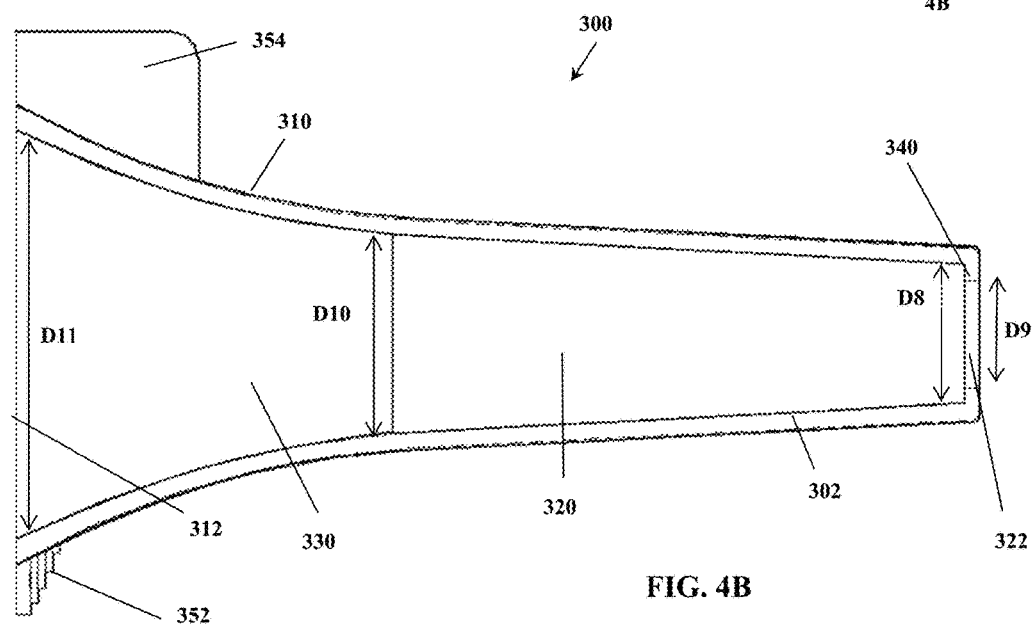
FIG. 4B is a cross-sectional view of one embodiment of the speculum tip taken along line 4B-4B from FIG. 4A.
Figure 4C:
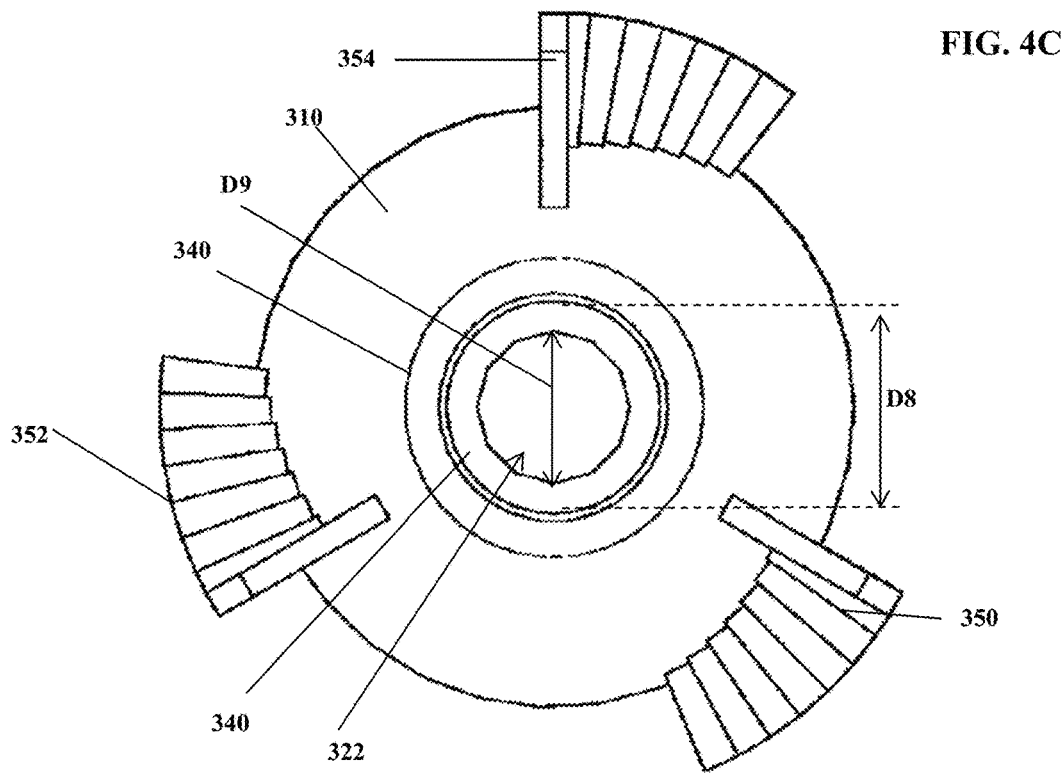
FIG. 4C is a front view of one embodiment of the speculum tip taken from view 4C from FIG. 4A.

Another embodiment of the speculum tip 300 is shown in FIGS. 4A-4D. Similar features and elements are present in the speculum tip 300 as in the speculum tips 100 and 200 with several slight variations. The speculum tip 300 includes a generally conical configuration with a narrow distal tip region 302 longitudinally extending from a larger proximal region 310. The distal tip region 302 generates a toroidal vortex by fluid traversing through a central shaft lumen 320 and a distal lumen lip 340 coaxially disposed within the distal tip region 302, as shown in FIG. 4B-4C. The distal end of the central shaft lumen 320 includes a distal lip 340 that surrounds a distal opening 322 as to create a smaller distal opening 322 compared to the distal end of the central shaft lumen 320. The central shaft lumen 320 includes a conical cross-section or profile that narrows to the distal opening 322. The central shaft lumen 320 includes trapezoidal cross-section or profile that includes a distal end larger than a proximal end. The distal opening 322 through which a constant toroidal vortex or focusing toroidal vortex displaces the eardrum without the requirement of a pressure seal of the ear canal. The proximal region 310 includes a proximal opening 312 operably coupled with a proximal lumen 330 disposed within the proximal region 310. The proximal lumen 330 includes a conical cross-section or profile that narrows to the central shaft lumen 320. The speculum tip 300 includes a plurality of flanges 350 surrounding the proximal end of the proximal region 310. The flanges 350 include a stepped portion 352 descending from the vertical lip 354. The flanges 350 are used to secure the speculum tip to an otoscope as to provide the user a grip-like structure to twist or rotate the speculum tip 100 about its longitudinal axis. The flanges 150 may be removed from the speculum tip 100 depending on the otoscope features for securement.

Figure 4D:
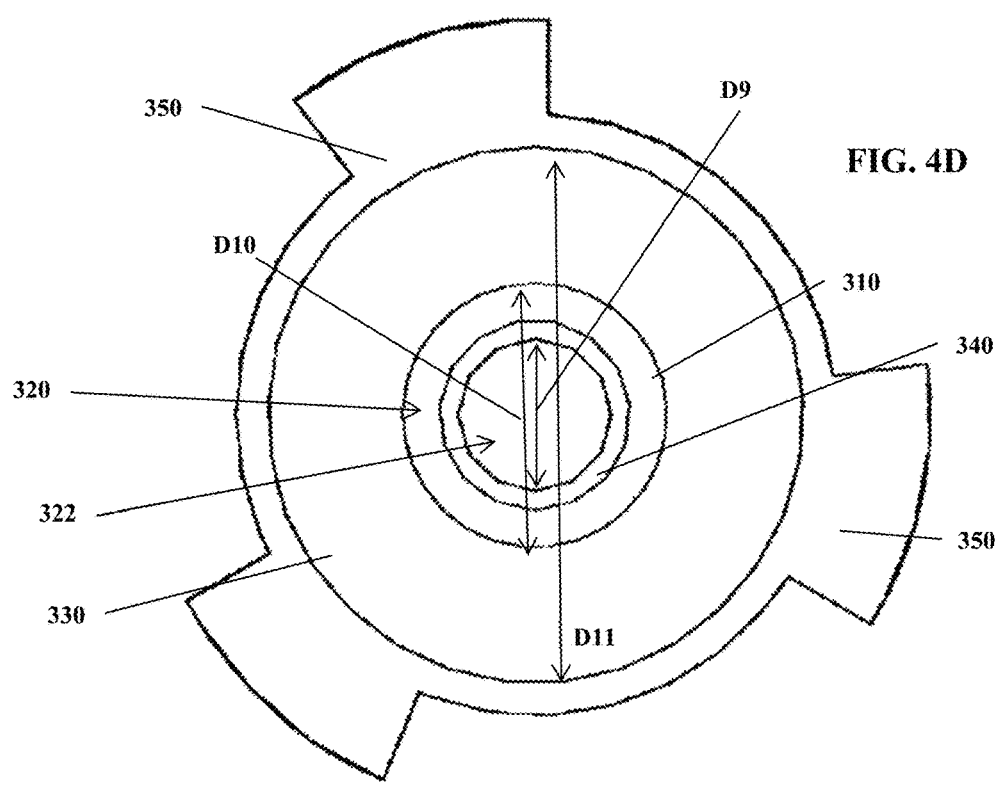
FIG. 4D is a back view of one embodiment of the speculum tip taken from view 4D from FIG. 4A.

In one embodiment, the walls of the central shaft lumen 320 are separated by about 0.1 to about 15 mm as to create the air vortex rings exiting the distal opening 322. The central shaft lumen 320 includes a diameter D8 that is narrowed by the distal end of the central shaft lumen 320, as shown in FIGS. 4B-4D. The distal lip 340 includes a diameter D9 that creates a smaller distal opening 322 than the diameter D8 of the distal end of the central shaft lumen 320, which produces a smaller diameter vortex ring. As such, the diameter D9 is smaller than the diameter D8. In one embodiment, an optimum ratio of D9 and D8 is: D9=D8/2. In other embodiments, the ration of D9 to D8 is between about D9=D8/4 to about D9=5(D8)/6.

The proximal lumen 330 includes a distal end with a diameter D10 that coaxially aligns with the proximal end of the central shaft lumen 320, as shown in FIG. 4B. The diameter D10 is larger or greater than the diameter D8 of the distal end of the central shaft lumen 320, such that the central shaft lumen 320 includes a generally trapezoidal cross-section or profile. The proximal lumen 330 includes a proximal end with a diameter of D11. The diameter D11 is larger or greater than the diameter D10 of the distal end of the proximal lumen 330, such that the proximal lumen 330 includes a generally curved cross-section shape or profile. A focusing toroidal vortex is generated by fluid passing through the proximal lumen 330, traversing the central shaft lumen 320, and exiting the distal opening 322.

Figure 5C:
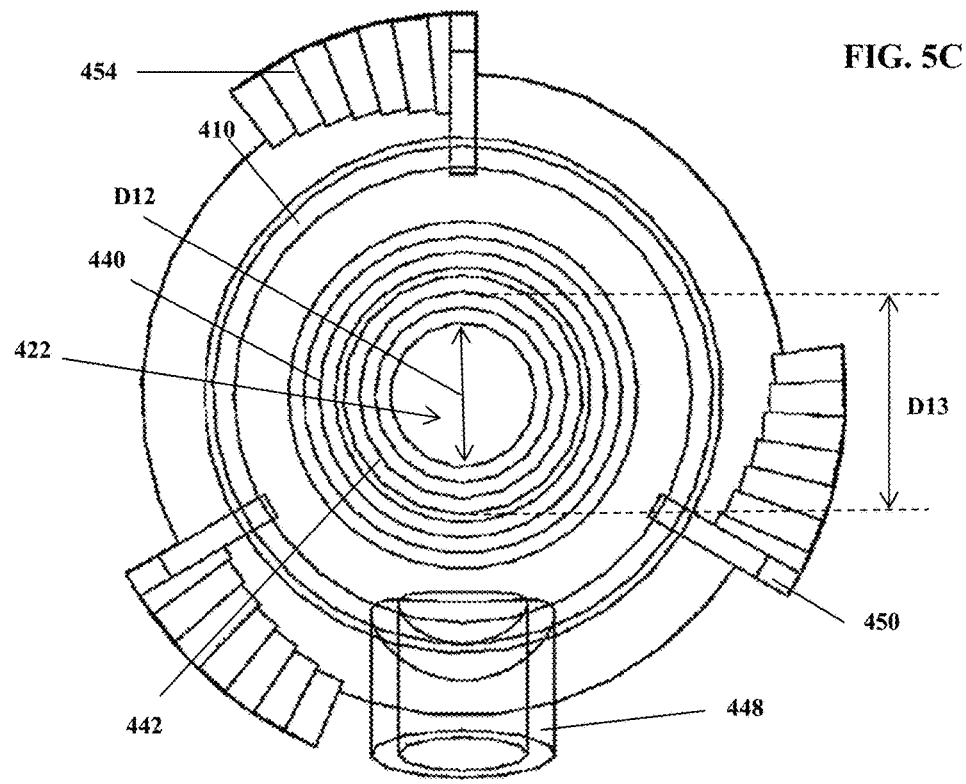
FIG. 5C is a front view of one embodiment of the speculum tip taken from view 5C from FIG. 5A.

Another embodiment of the speculum tip 400 is shown in FIGS. 5A-5D. Similar features and elements are present in the speculum tip 400 as in the speculum tips 100-300 with several slight variations. The speculum tip 400 includes a generally conical configuration with a narrow distal tip region 402 longitudinally extending from a larger proximal region 410. The distal tip region 402 includes a coaxially disposed central shaft lumen 420. The proximal region 410 includes a proximal lumen 430. A second outer lumen 440 coaxially surrounds the central shaft lumen 420 and the proximal lumen 430 and extends from a portion of the proximal region 410. The outer lumen 440 generates a double-concentric toroidal vortex by fluid traversing through the outer lumen 440, as shown in FIG. 5B-5C. The distal end of the central shaft lumen 420 includes a distal opening 422 and the distal end of the second outer lumen 440 includes a distal outer opening 442. The central shaft lumen 420 and the proximal lumen 430 include a conical cross-section or profile that narrows to the distal opening 422. The second outer lumen 440 is fluidly coupled with an outer port 448 disposed on the exterior surface of the proximal region 410. The distal outer opening 442 generates a toroidal vortex that displaces the eardrum without the requirement of a pressure seal of the ear canal. The distal outer opening 442 generates a greater impulse and evenly distributed impulse, and the different toroid shape due to the ring outlet will displace the tympanic membrane for a stronger and safer modulation. The proximal region 410 includes a proximal opening 412 operably coupled with the proximal lumen 430 coaxially disposed within the proximal region 410. The proximal lumen 430 includes a conical cross-section or profile that narrows to the central shaft lumen 420. The second outer lumen 440 includes a second proximal opening 442 fluidly coupled with the proximal lumen 430. The second outer lumen 440 includes conical cross-section or profile that narrows to the distal outer opening 442. The speculum tip 400 includes a plurality of flanges 450 surrounding the proximal end of the proximal region 410. The flanges 450 include a stepped portion 452 descending from the vertical lip 454. The flanges 450 are used to secure the speculum tip to an otoscope as to provide the user a grip-like structure to twist or rotate the speculum tip 100 about its longitudinal axis. The flanges 150 may be removed from the speculum tip 100 depending on the otoscope features for securement.

Figure 5D:
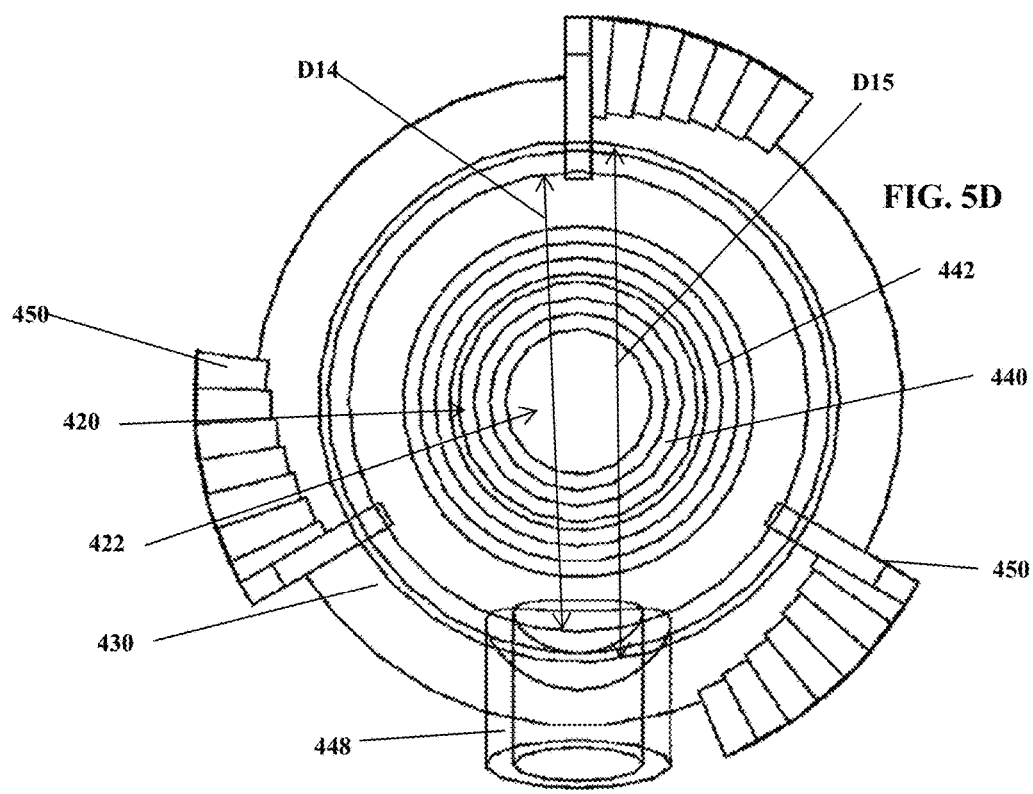
FIG. 5D is a back view of one embodiment of the speculum tip taken from view 5D from FIG. 5A.

In one embodiment, the walls of the central shaft lumen 420 are separated by about 0.1 to about 15 mm as to create the double-curling air vortex ring exiting the distal outer opening 442. The central shaft lumen 420 includes a diameter D13 that is narrowed by the distal end of the central shaft lumen 420, as shown in FIGS. 5B-5D. The distal outer opening 442 includes a diameter D12 that creates a larger circular opening than the diameter D13 of the distal end of the central shaft lumen 420, as to produce a double-curling air vortex ring. As such, the diameter D12 is smaller than the diameter D13.

The proximal lumen 430 includes a distal end with a diameter D15 that coaxially aligns with the proximal end of the central shaft lumen 420, as shown in FIG. 5B. The diameter D15 is larger or greater than the diameter D13 of the distal end of the central shaft lumen 420, such that the central shaft lumen 420 includes a generally trapezoidal cross-section or profile. The second outer lumen 440 includes a proximal outer opening 442 with a diameter of D14. The diameter D14 is larger or greater than the diameter D12 of the distal end of the second outer lumen 440, such that the second outer lumen 440 includes a generally curved cross-section shape or profile. D12 includes a diameter to allow for sufficient field-of-view for imaging and also D12 includes a diameter that is structurally sound to interface and administer the pneumatic pulse without structural issues/failure. The double-curling toroidal vortex is generated by fluid passing through the inlet 452, traversing the second outer lumen 440, and exiting the distal outer opening 442. The drag forces from the inner and outer diameter surfaces along the second outer lumen 440 cause the double-curling behavior of the toroidal vortex.

Figure 6A:
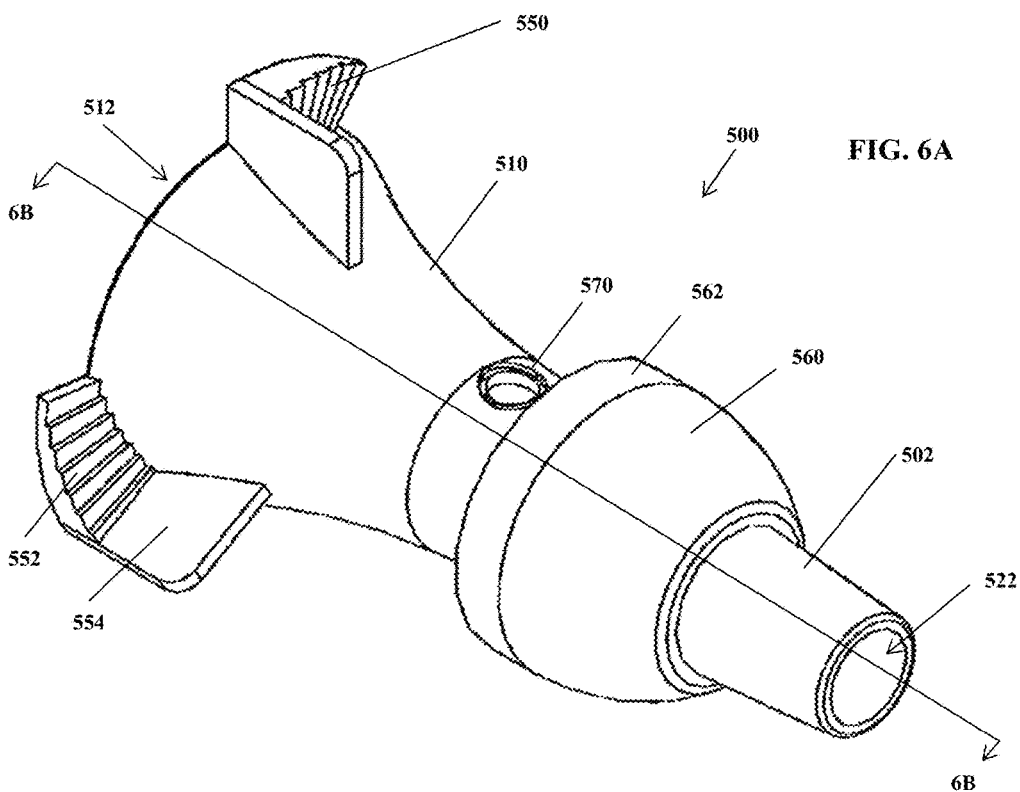
FIG. 6A is a perspective view of one embodiment of the speculum tip.
Figure 6B:
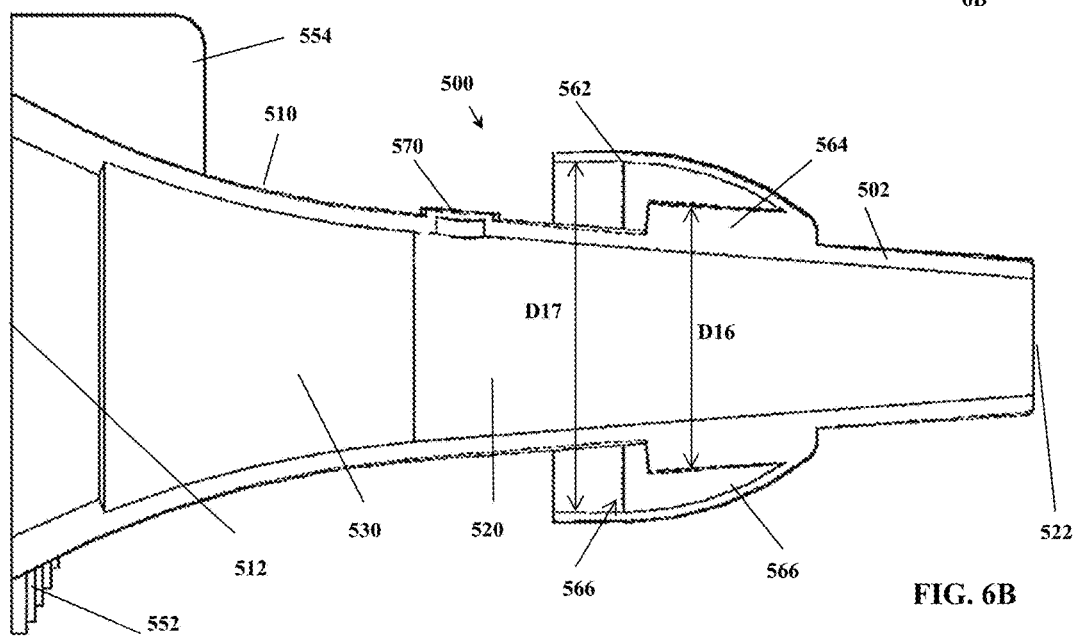
FIG. 6B is a cross-sectional view of one embodiment of the speculum tip taken along line 6B-6B from FIG. 6A.

Another embodiment of the speculum tip 500 is shown in FIGS. 6A-6B. Similar features and elements are present in the speculum tip 500 as in the speculum tips 100-400 with an additional sealing feature 560. Any of the previous speculum tips 100-400 may include a sealing feature 560 if the toroidal vortex is unable to be generated for any reason, or has superior structural integrity when a sealing feature is incorporated. Difficulties in generating the toroidal vortex may range from canal anatomy, earwax protrusions, or pneumatic malfunctions in the otoscope. The sealing feature 560 is coaxially disposed around the exterior surface of the distal tip region 502. The sealing feature 560 made of such material as silica gel or memory foam, and is integrated into the speculum tip 500 to ensure a quick and easy seal of the ear canal of the patient. Alternative materials include (b) polymers, such as polyvinylchloride, nylon, polytetrafluoroethylene, polystyrene, acrylonitrile-butadiene styrene, polypropylene, and other suitable plastics; or (c) ceramics, such as silicon carbide, tungsten carbide, apatite, and other suitable ceramics; wherein the suitable metals, alloys, plastics, or ceramics respectively have a tensile strength sufficient to maintain a tubular structure and are capable of being sterilized for medical use. The sealing feature 560 may be designed in different sizes: a smaller diameter model with less distance between the sealing feature 560 and distal end of the tip for infants and young children, as well as a standard, larger model, with more distance between the sealing feature 560 and distal end of the tip, to accommodate deeper ear canals found in older ears. The sealing feature 560 includes a lip region 562 coaxially extending around a distal shaft region 564, which creates a lipped lumen 566 between the distal shaft region 564 and the exterior surface of the distal tip region 502. The lip region 566 axially moves towards the exterior surface of the distal tip region 502 when the speculum tip 500 is disposed within an ear canal. The lipped region 562 is biased to extend axially away from the exterior surface of the distal tip region 502 as to create a seal against the ear canal. The lipped region 562 may include elastic or superelastic materials that provide resistance to mechanical deformation. The lip region 562 includes a diameter D17 and the distal shaft region 564 includes a diameter D16. The diameter D17 is greater than the diameter D16 as to create the lipped lumen 566 between the distal shaft region 564. The distal shaft region 564 is secured to the exterior surface of the distal tip region.

As shown in FIGS. 6A-6B, the speculum tip 500 includes a thin membrane 570 traversing the thickness of the distal tip region 502. The thin membrane 570 functions as a pneumatic fuse in and designed to give way before enough pressure would be delivered to damage the eardrum. A user may potentially damage the eardrum with an absolute seal of the canal, when compared to the poor seals currently available. The thin membrane may include a diameter of about 2 mm, which will burst or unseal when the pressure builds up in the ear canal about a particular threshold limit.

The speculum tip 500 includes a generally conical configuration with a narrow distal tip region 502 longitudinally extending from a larger proximal region 510. The distal end of the central shaft lumen 520 includes a distal opening 522 through which a delivered puff of fluid displaces the eardrum. The proximal region 510 includes a proximal opening 512 operably coupled with a proximal lumen 530 disposed within the proximal region 510. The proximal lumen 530 includes a conical cross-section or profile that narrows to the central shaft lumen 520. The speculum tip 500 includes a plurality of flanges 550 surrounding the proximal end of the proximal region 510. The flanges 550 include a stepped portion 552 descending from the vertical lip 554. The flanges 550 are used to secure the speculum tip to an otoscope as to provide the user a grip-like structure to twist or rotate the speculum tip 100 about its longitudinal axis. The flanges 150 may be removed from the speculum tip 100 depending on the otoscope features for securement.

EXAMPLES

The following examples are put forth so as to provide those of ordinary skill in the art with a complete disclosure and description of how the systems, articles, devices, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Airflow Requirement to Achieve Noticeable Displacement of the Eardrum in the Speculum Tips Speculum tips 100-500 are tested to determine the requirements and limitations of use of the designs. Each prototype will be used to deliver bursts of air to a synthetic eardrum located ~5 mm away from the speculum tip, similar to the clinical use case. Multiple dynamic stimuli, including a traditional pneumatic insufflation bulb and various sizes of plunger syringes will be used to deliver a known volume of air between 0.25-5 cc delivered at pressure between about 10 mmHg and 100 mmHg over a known duration to determine the flow required to achieve visible displacement of the synthetic membrane. The known duration may be between about 50 ms to about 1000 ms. Each Speculum tip 100-500 will be compared to evaluate performance, with total membrane displacement as a key metric. Once these data are taken, analysis to determine the suitability of using a traditional pneumatic insufflation bulb with the Speculum tips 100-500 will be performed. It will be important to determine whether separate stimulus will be needed to produce the required displacement or whether our product can be used with existing pneumatic insufflation bulbs.

Figure 7:
FIG. 7 is a photograph of the Life/form pneumatic otoscopy kit, which will enable experimental testing of speculum tips.
Figure 9A:
FIG. 9A is a photograph of pediatric and adult standard disposable tips.
Figure 9B:
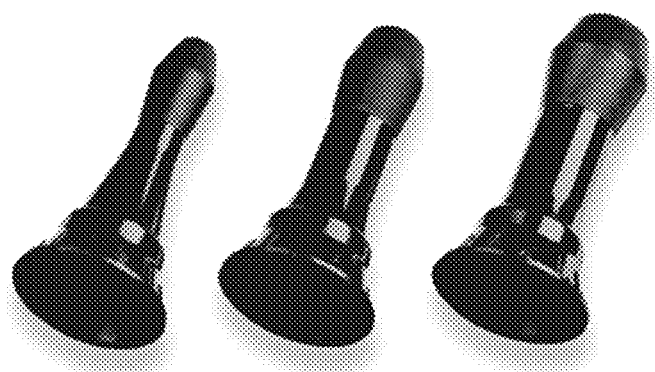
FIG. 9B is a photograph of Welch Allyn's recently introduced SofSpec tip.

The Displacement Induced by the Speculum Tips 100-500 Compared to that Induced by Traditional Pneumatic Methods Using a Standard or SofSeal Speculum The purpose of the pneumatic exam is to displace the eardrum and qualitatively assess the amount of motion to determine the pressure in the middle ear. It is therefore important to quantitatively compare each Speculum tip's 100-500 ability to displace a synthetic membrane and compare each to current commercial solutions. For this experiment, the Life/form ear model, as shown in FIG. 7, will be utilized and each of the Speculum tips 100-500, as well as a standard otoscope speculum (FIG. 9A) and Welch Allyn's SofSpec product (FIG. 9B) will be used to displace the membrane. The Life/form ear model instructions can be found at http://www.globalnasco.com/pdfs/Health_Care/manuals/LF01090.pdf, herein incorporated by reference in its entirety. The Speculum tips 100-500 will not rely on a seal of the ear canal; while the standard and SofSeal specula (FIG. 9B) will be operated as they are meant to, requiring a seal of the ear canal. The membrane displacement will be measured using an OCT imaging system, as described in U.S. Pat. Nos. 8,115,934 and 8,594,757, herein incorporated by reference in their entireties. This imaging system is capable of detecting deflections on the order of ~5 microns and will be responsible for measuring the amount of displacement from each speculum tip. This will allow a true quantitative comparison of each tip. The imaging will be done from the middle ear side of the synthetic membrane, while the air stimulus will come from the ear canal side of the membrane.

Sealing Feature Providing a Better Seal of the Ear Canal

A direct and quantitative comparison of silica gel and memory foam may determine which will be best for sealing the ear canal. Crafting an experiment to use each speculum tip on an anatomically correct pediatric ear model will assess which material is better suited to this application. An anatomic model called the Life/form pneumatic otoscopy kit (FIG. 7) will be used to evaluate the technologies proposed in this application.

Figure 8:
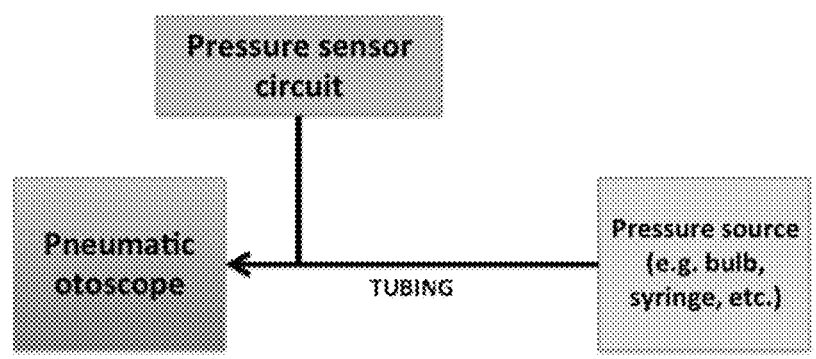
FIG. 8 is a schematic of the proposed system design for monitoring ear canal pressure in real time.

For this experiment, an insufflation bulb using standard pneumatic techniques will modulate the ear canal pressure in the Life/form model as shown in FIG. 7. A calibrated pressure sensor will be connected to the system in a 'T' configuration, as shown in FIG. 8, to monitor the canal pressure in real time. After ensuring the system has no leaks aside from potential leaks due to poor sealing of the canal, the seal quality will be quantified by measuring how quickly the pressurized canal loses pressure. This will allow quantitative comparison of the proposed models with each other, as well as existing solutions.

How Much Improvement is Obtained by Using the Sealing Feature 560 Over Standard and SofSeal Specula?

Using the experimental setup previously described in FIG. 8, a quantitative comparison of the Sealing Feature 560 will be made with traditional commercial otoscope tips and the Welch Allyn SofSeal pneumatic tips. Angle of insertion will be varied in this comparison, and time to obtain a seal will be measured, as this is a critical parameter to the time-constrained physician.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

What is claimed is:

1. A speculum tip comprising:
a cylindrical configuration including a narrow distal tip region longitudinally extending from a larger proximal region, wherein the distal tip region generates a toroidal vortex throughout a central shaft lumen coaxially disposed within the distal tip region; a distal end of the central shaft lumen includes a distal opening from which the toroidal vortex travels to displace a membrane; the proximal region includes a proximal opening operably coupled with a proximal lumen coaxially disposed within the proximal region as to receive a pulse of fluid.

2. The speculum tip of claim 1, wherein the proximal lumen includes a cylindrical cross-section that narrows to a middle lumen, whereby the middle lumen transitions to the central shaft lumen.

3. The speculum tip of claim 2, wherein the central shaft lumen includes a diameter D1, and D1 is between about 0.1 to about 15 mm as to create the toroidal vortex exiting the distal opening.

4. The speculum tip of claim 3, wherein the diameter D1 produces a constant toroidal vortex with a diameter between about 0.1 to about 15 mm.

5. The speculum tip of claim 4, wherein the proximal lumen includes a proximal end with a diameter of D2 and the proximal lumen includes a distal end with a diameter of D3, wherein the diameter D2 is greater than the diameter D3, such that the proximal lumen includes a generally curved cross-section profile, and the diameter D2 is formatted as to fit a pneumatic otoscope and a pressure generator to generate the pulse of fluid.

6. The speculum tip of claim 1, wherein the distal end of the central shaft lumen is coupled to a proximal end of a distal lumen; the central shaft lumen includes a conical cross-section that narrows to the distal lumen; the distal lumen includes trapezoidal cross-section that includes a distal end larger than a proximal end; the distal end of the distal lumen includes the distal opening to generate an expanding toroidal vortex.

7. The speculum tip of claim 6, wherein the distal lumen includes an expanded tip cross-section, where the distal end of the distal lumen includes a diameter D4; the distal end of the central shaft lumen narrows to a diameter D5, wherein the distal end of the central shaft lumen coaxially aligns with the proximal end of the distal lumen; and the narrowing of the central shaft lumen to diameter D5 to generate the expanding toroidal vortex; and the diameter D4 is larger than the diameter D5.

8. The speculum tip of claim 7, wherein a proximal lumen includes a distal end with a diameter D6 that coaxially aligns with the proximal end of the central shaft lumen; the proximal lumen includes a proximal end with a diameter of D7; and the diameter D7 is larger or greater than the diameter D6 of the distal end of the proximal lumen, such that the proximal lumen includes a generally curved cross-section shape.

9. The speculum tip of claim 1, further comprising a second outer lumen coaxially surrounding the central shaft lumen and a proximal lumen extending from a portion of the proximal region; wherein the second outer lumen generates a double-concentric toroidal vortex by fluid traversing through the outer lumen and the central shaft lumen; a distal end of the second outer lumen includes a distal outer opening.

10. The speculum tip of claim 9, wherein the second outer lumen is fluidly coupled with an outer port disposed on the exterior surface of the proximal region.

11. The speculum tip of claim 10, wherein the central shaft lumen includes a diameter D13 that is narrowed by the distal end of the central shaft lumen; the distal outer opening includes a diameter D12 that creates a larger circular opening than the diameter D13 of the distal end of the central shaft lumen.

12. A speculum tip, comprising:
a cylindrical configuration including a narrow distal tip region longitudinally extending from a larger proximal region, wherein the distal tip region generates a toroidal vortex throughout a central shaft lumen coaxially disposed within the distal tip region; a distal end of the central shaft lumen includes a distal opening from which the toroidal vortex travels to displace a membrane; the proximal region includes a proximal opening operably coupled with a proximal lumen coaxially disposed within the proximal region as to receive a pulse of fluid, where the distal tip region includes a distal lumen lip coaxially disposed within the distal tip region; and the distal end of the central shaft lumen is coaxially coupled with the distal lip that surrounds the distal opening as to create a smaller distal opening than to the distal end of the central shaft lumen through which a focusing toroidal vortex displaces the eardrum without the requirement of a pressure seal of the ear canal.

13. The speculum tip of claim 12, wherein the central shaft lumen includes a diameter D8 that is narrowed by the distal end of the central shaft lumen; the distal lip includes a diameter D9 that creates a smaller distal opening than the diameter D8 of the distal end of the central shaft lumen, which produces a focusing diameter vortex ring.

14. The speculum tip of claim 13, wherein the diameter D9 is smaller than the diameter D8, and the ratio of D9:D8 is selected at ratio between about 1/4 and about 5/6.

15. A method of generating a toroidal vortex for a speculum tip, comprising the steps:
    generating a toroidal vortex through a speculum tip comprising a cylindrical configuration with a narrow distal tip region longitudinally extending from a larger proximal region;
    passing a pulse of fluid through a generally central shaft lumen coaxially disposed within the distal tip region and a distal opening on a distal end of the central shaft lumen; and
    displacing a membrane by the toroidal vortex exiting the distal opening without the requirement of a pressure seal of the ear canal.

16. The method of claim 15, further comprising:
    coupling the proximal region to an otoscope and a pressure generator.

17. The method of claim 16, further comprising selecting a diameter D1 of the central shaft lumen to produce a constant diameter toroidal vortex.

18. The method of claim 17, wherein the toroidal vortex includes a fluid burst of at least about 5 mmHg to about 100 mmHg to displace the tympanic membrane; and
    diagnosing otitis media.

19. The method of claim 18, further comprising:
    imaging the tympanic membrane with an Optical Coherence Tomography system.

20. The method of claim 19, wherein the toroidal vortex is selected from the group consisting of an expanding toroidal vortex, a focusing toroidal vortex, a constant diameter toroidal vortex, and a double concentric toroidal vortex.

* * * * *